United States Patent [19]

Guillaumet et al.

[11] Patent Number: 5,155,116
[45] Date of Patent: Oct. 13, 1992

[54] MEDICINAL OXAZOLOPYRIDINE COMPOUNDS

[75] Inventors: Gérald Guillaumet, Orleans; Christine Flouzat, Clermont; Daniel H. Caignard, Paris; Pierre Renard, Versailles; Michelle Devissaguet; Béatrice Guardiola, both of Neuilly sur Seine, all of France

[73] Assignee: Adir et Compagnie, Courbevoie, France

[21] Appl. No.: 711,297

[22] Filed: Jun. 6, 1991

[30] Foreign Application Priority Data

Jun. 29, 1990 [FR] France ................. 90 08202

[51] Int. Cl.⁵ .................. A61K 31/435; C07D 498/04
[52] U.S. Cl. ................. 514/234.2; 514/253; 514/302; 544/127; 544/362; 546/116
[58] Field of Search ............. 546/116; 544/127, 362; 514/234.2, 253, 302

[56] References Cited

PUBLICATIONS

Rüfenact et al., Helvetica Chimica Acta, vol. 59(5) pp. 1593-1612 (1976).

*Primary Examiner*—Bernard Dentz
*Attorney, Agent, or Firm*—Gordon W. Hueschen

[57] ABSTRACT

Compounds of general formula (I):

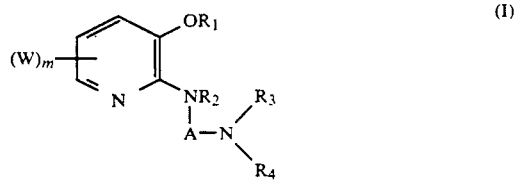

in which:

$R_1$ and $R_2$ each represent a hydrogen atom or, with the nitrogen and oxygen which bear them, form an —O—CO—N link, W represents a halogen atom or a lower alkyl or alkoxy group optionally substituted with one or more halogen atoms, such as trifluoromethyl, and m being between 0 and 3, A is a linear or branched alkyl radical comprising from 1 to 6 carbon atoms, $R_3$ and $R_4$ are defined in the description have medicinal properties.

14 Claims, No Drawings

MEDICINAL OXAZOLOPYRIDINE COMPOUNDS

The present invention relates to new oxazolo[4,5-b]pyridine compounds, to a process for preparing these and to pharmaceutical compositions containing them.

The properties, both analgesic and anti-inflammatory, of 2-phenyl-3H-oxazolo[5,4]- and -[4,5]pyridines are already known (Patents U.S. Pat. No. 4,038,396, FR 2,328,471, FR 2,319,354, GB 1,421,619).

However, these products possess an essentially anti-inflammatory profile, as confirmed by the therapeutic indications mentioned in the patents cited above, or else have the drawback of not dissociating the two types of activity: analogesic on the one hand, antipyretic and anti-inflammatory on the other hand.

The applicant has now discovered new compounds exhibiting a good level of analgesic activity but possessing the especially advantageous feature of being completely devoid of anti-inflammatory activity: the compounds of the present invention are, in effect, endowed with a high level of pure analgesic activity. It is the case that most non-morphinic analgesic substances known to date also posses anti-inflammatory activity (for example salicyl derivatives, pyrazole derivatives, etc.), and they consequently intervene in the processes occurring in inflammation. These processes involve a very large number of chemical mediators (prostaglandins, thromboxane A2, etc.); multifarious side-effects accordingly ensue, the best known of these being attack of the gastric mucosa with a possibility of ulcers, and inhibition of platelet aggregation with disorders of coagulation. Apart from the disturbances they cause, these concomitant effects prohibit the use of these products in many subjects who are especially sensitive to them. Being devoid of all anti-inflammatory activity, the compounds of the present invention hence do not interfere with the mediators of inflammation, and are hence devoid of the side-effects mentioned above. This feature, combined with their complete absence of toxicity and their high level of activity, renders the compounds of the present invention usable as an analgesic much more safely and without the restrictions in their use customarily known for the large majority of these products. In addition, some products of the invention have evinced an affinity for muscarine receptors, which distinguishes them completely from the prior art.

More specifically, the invention relates to compounds of general formula (I):

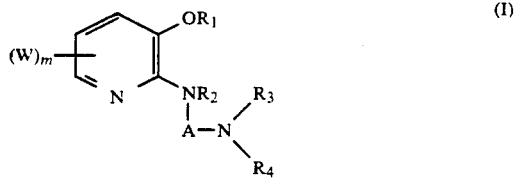

in which:
 $R_1$ and $R_2$ each represent a hydrogen atom or, with the nitrogen and oxygen which bear them, form an —O—CO—N link,
 W represents a halogen atom or a lower alkyl or alkoxy group optionally substituted with one or more halogen atoms, such as trifluoromethyl, and m being between 0 and 2,
 A is a linear or branched alkyl radical comprising from 1 to 6 carbon atoms,
 $R_3$ and $R_4$, which may be identical or different, represent;
  a hydrogen atom,
  a linear or branched lower alkyl group,
  a linear or branched lower alkenyl group,
  a cycloalkyl group having 6 to 10 carbon atoms,
  an aryl or (lower alkyl)aryl or aryl(lower alkyl) group,
 each of these groups being unsubstituted or substituted with one or more halogen atoms or trifluoromethyl, hydroxyl or lower alkoxy groups, or alternatively:
  $R_3$ and $R_4$, with the nitrogen atom to which they are linked, constitute a saturated or unsaturated, mono- or bicycle nitrogenous heterocyclic system comprising at most 12 atoms—not counting the hydrogen atoms—among which may be included one to three hetero atoms selected from nitrogen, oxygen and sulfur, unsubstituted or substituted with a lower alkyl or phenyl or phenyl(lower alkyl) or diphenyl(lower alkyl) group, it being possible for the phenyl, phenyl(lower alkyl) or diphenyl(lower alkyl) groups to be substituted with one or more halogen atoms or hydroxyl, lower alkyl, lower alkoxy or trifluoromethyl groups, on condition that $R_3$ and $R_4$, with the nitrogen atom to which they are linked, do not constitute a 4-arylpiperazine or 4-heteroarylpiperazine system, on the understanding that lower alkyl, lower alkenyl or lower alkyloxy radical is understood to mean a linear or branched group comprising from 1 to 6 carbon atoms, and that aryl or heteroaryl groups are understood to mean unsaturated mono- or bicyclic groups comprising from 5 to 12 carbon atoms—not counting the hydrogen atoms—incorporating or otherwise in their carbon skeleton one, two or three hetero atoms selected from nitrogen, oxygen and sulfur, their isomers, epimers and diastereoisomers, as well as their addition salts with a pharmaceutically acceptable acid and, when $R_1$ and $R_2$ each represent a hydrogen atom, their addition salts with a pharmaceutically acceptable base.

Among acids which may be added to the compounds of formula (I) to form an addition salt, hydrochloric, sulfuric, phosphoric, tartaric, malic, maleic, fumaric, oxalic, methanesulfonic, ethanesulfonic, camphoric, citric, etc., acids may be mentioned by way of example.

Among bases which may be added to the compounds of formula (I) for which $R_1$ and $R_2$ each represent a hydrogen atom, alkali metal hydroxides, alkali metal salts, etc., may be mentioned by way of example.

The invention also encompasses the process for obtaining compounds of formula (I), wherein a compound of formula (II):

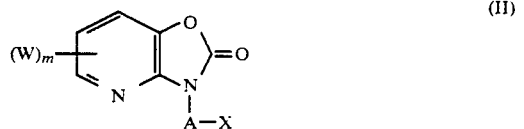

in which W, m and A have the same meaning as in the formula (I) and X represents a halogen atom, is reacted, preferably under an inert atmosphere, with a compound of formula (III), preferably in excess:

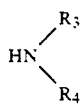 (III)

in which $R_3$ and $R_4$ have the same meaning as in the formula (I), in an organic medium in the presence of a basic agent and at a temperature between room temperature and the refluxing temperature of the chosen solvent, to lead, after cooling, extraction and, where appropriate, purification, to a compound of formula (I/A):

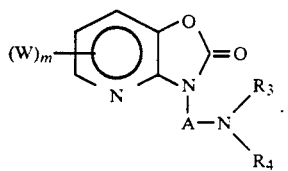 (I/A)

a special case of the compounds of formula (I) for which $R_1$ with $R_2$ forms a C=O group, which may, if so desired, be separated, where applicable, into its isomers and then salified with a pharmaceutically acceptable acid, which compound of formula (I/A) may be treated, if so desired, with an alkaline agent in aqueous solution, at a temperature between room temperature and the boiling point of the reaction medium, to lead, where appropriate after acidification and/or neutralization of the reaction medium, to a compound of formula (I/B):

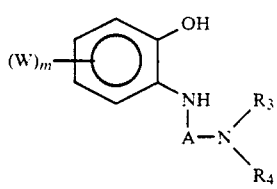 (I/B)

a special case of the compounds of formula (I) in which $R_1$ and $R_2$ each represent a hydrogen atom and W, m, A, $R_3$ and $R_4$ have the same meaning as above, which is purified, if necessary, by a technique selected from crystallization and chromatography and which is salified, if so desired, with a pharmaceutically acceptable acid or base.

The compounds of formula (II) may be obtained by reacting a compound of formula (IV):

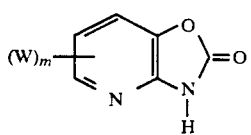 (IV)

in which W and m have the same meaning as in the formula (I), with an alkali metal hydroxide in an aqueous medium or an alkali metal alcoholate in an organic medium, to lead to a derivative of formula (V):

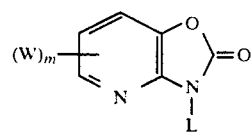 (V)

in which W and m have the same meaning as above and L represents an alkali metal, which is condensed with a compound of formula (VI):

$$X-A-X' \quad (VI)$$

in which A has the same meaning as above and X and D', which may be identical or different, each represent a halogen atom, preferably under an inert atmosphere, in an organic medium at a temperature between room temperature and the refluxing temperature of the chosen solvent, to lead, after, where appropriate, extraction and purification by chromatography and/or crystallization, to the compound of formula (II).

The compounds of formula (I/A) may also be obtained by condensation of a compound of formula (V) as shown above with a compound of formula (VII):

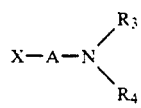 (VII)

in which X, A, $R_3$ and $R_4$ have the same meaning as above, in an organic medium at a temperature between room temperature and the refluxing temperature of the chosen solvent, to lead, after, where appropriate, cooling, extraction and purification, to a compound of formula (I/A) as defined above, the isomers of which, where applicable, are separated and which is salified, if so desired, with a pharmaceutically acceptable acid.

The compounds of formula (VII) will advantageously be obtained by condensation of a compound of formula (VI) as defined above with an amine of formula (III) as defined above, preferably under an inert atmosphere, in an organic medium at a temperature between room temperature and the refluxing temperature of the chosen solvent, to lead, after, where appropriate, extraction and purification, to a compound of formula (VII).

A special case of the compounds of the present invention consists of the compounds of formula (I) in which A is a methylene link —$CH_2$—.

These compounds will advantageously be obtained in a single step by dissolving a compound of formula (IV), a slight excess of an amine of formula (III) and an excess of formaldehyde in a lower aliphatic alcohol medium, and heating the solution thereby obtained to a temperature between room temperature and the boiling point of the solution, to lead, after, where appropriate, cooling, allowing the mixture to stand for one to two hours, filtration and, where appropriate, chromatography on a silica column, to a compound of formula (I/A1):

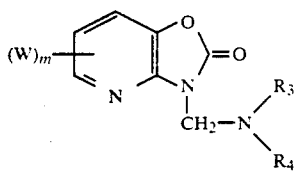

a special case of the compounds of formula (I/A) in which A is a methylene link —CH$_2$— and in which W and m have the same meaning as in the formula l(I), which may be salified, if so desired, with a pharmaceutically acceptable acid and converted, if so desired, to a compound (I/B1):

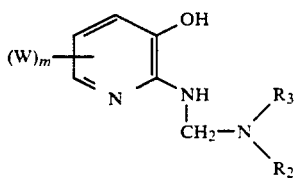

a special case of the compound of formula (I/B) in which A is a methylene link CH$_2$ and W and m have the same meaning as in the formula (I), by treatment of a compound of formula (I/A1) with an alkaline agent in aqueous solution as described for the conversion of the compounds of formula (I/A) to a compound of formula (I/B).

The compounds of formula (I) possess advantageous pharmacological properties.

In particular, these compounds have evinced advantageous analgesic activity.

A pharmacological study of the compounds of the invention showed that they were of low toxicity, endowed with a high level of pure analgesic activity, devoid of an anti-inflammatory component and hence devoid of drawbacks inherent in most compounds exhibiting this activity (ulcerogenic action on the mucosi, interference with coagulation, etc.). This spectrum of activity hence renders the compounds of the present invention especially advantageous in a number of indications such as rheumatic pain such as that associated with sprains, fractures and dislocations, post-traumatic pain, postoperative pain, dental pain, neurological pain such as facial neuralgia, visceral pain such as nephritic colic, dysmenorrhea, proctological surgery, pancreatitis, diverse pains, headache, cancer pain, etc.

In addition, the compounds of the invention have evinced a good affinity for MI receptors. This means that they may be used profitably in disorders of cerebral circulatory insufficiency, the multifarious disorders resulting from normal or pathological aging, memory loss and Alzheimer's disease.

The subject of the present invention is also pharmaceutical compositions containing the products of formula (I) or one of their addition salts with a pharmaceutically acceptable acid, alone or in combination with one or more pharmaceutically acceptable, non-toxic, inert excipients or vehicles.

Among the pharmaceutical compositions according to the invention, there may be mentioned, more especially, those which are suitable for oral, parenteral, nasal, rectal, perlingual, ocular or respiratory administration, and in particular injections, aerosols, eye or nasal drops, simple or sugar-coated tablets, sublingual tablets, sachets, packets, hard gelatin capsules, sublingual preparations, troches, suppositories, creams, ointments, skin gels, and the like.

The appropriate dosage varies according to the patient's age and weight, the administration route and the nature of the therapeutic indication and of any associated treatments, and ranges between 1 centigram and 4 grams per 24 hours.

The examples which follow illustrate the invention and in no way limit it.

The $^1$H nuclear magnetic resonance spectra were recorded using TMS as an internal reference. The infrared spectra were recorded using a KBr disk containing approximately 1% of the test product.

The products obtained according to the procedures described under the heading "Preparations" do not form part of the invention; they nevertheless constitute synthesis intermediates useful for the preparation of the compounds of the invention.

PREPARATIONS

Preparation 1: 3H-Oxazolo[4,5-b]pyridin-2-one* (See Appendix)

5.5 g (0.05 mol) of 2-amino-3-hydroxypyridine are introduced into a three-necked flask and the system is placed under argon. 100 ml of anhydrous tetrahydrofuran (THF) are added. 12.15 g (0.075 mol) of 1,1-carbonyldiimidazole are then introduced. The mixture is heated to reflux for 5 hours (under argon). The THF is then evaporated off. The residue is taken up with dichloromethane. Washes of the organic phase are performed with NaOH solution (5%) (6×150 ml); the cyclized product passes into the aqueous phase and is precipitated at a pH in the region of 5 (by adding 2N hydrochloric acid solution). The product is filtered off and stored in a desiccator.

Yield: 77%

Melting point: 212°–214° C.

Preparation 2:5-Methyl-3H-Oxazolo[4,5-b]Pyridin-2-One* (See Appendix)

Stage A: 2-Nitro-3-Hydroxy-6-Methylpyridine 5.45 g (50 mmol) of 5-hydroxy-2-methylpyridine are added to 20 ml of concentrated sulfuric acid while cooling in an ice bath. The temperature is maintained at +6° C. and 2.35 ml of fuming nitric acid are added with stirring. The mixture is left overnight at room temperature. 100 g of ice are added with stirring. The product is filtered off, rinsed with water and dried.

Stage B: 2-Amino-3-Hydroxy-6- Methylpyridine 3.5 g of 2-nitro-3-hydroxy-6-methylpyridine are placed under a hydrogen pressure in 50 ml of methanol in the presence of 1 gram of palladinized charcoal. The mixture is stirred and filtered. The methanol is evaporated off.

Stage C: 5-Methyl-3H-Oxazolo[4,5-b]Pyridin-2-One 1.24 g (10 mmol) of 2-amino-3-hydroxy-6-methylpyridine are introduced into a three-necked round-bottomed flask. The contents are placed under argon. 20 ml of anhydrous tetrahydrofuran and then 2.43 g (15 mmol) of 1,1-carbonyldiimidazole are added. The mixture is heated to reflux for 6 hours. The reaction medium is evaporated. The crystals obtained are washed with water, filtered off and redissolved in hot methanol. The solution is filtered and re-evaporated.

Yield: 75%
Melting point: 243° C.
Spectral characteristics:

$^1$H NMR Solvent CDCl$_3$: δ ppm δ: 12.3 1H, unresolved complex, NH δ: 7.5 1H; doublet; H$_7$; J=8 Hz δ: 6.9 1H; doublet: H$_6$; J=8 Hz δ: 2.4 3H; singlet; CH$_3$ Infrared: 1750 cm$^{-1}$, ν (C=O) 1610 cm$^{-1}$, ν (C=C)

Preparation 3:
3-(2-Bromoethyl)-3H-Oxazolo[4,5-b]Pyridin-3-One

Stage A: Oxazolo[4,5-b]Pyridin-2-One Sodium Derivative 6 g (44.11 mmol) of 3H-oxazolo[4,5-b]pyridin-2-one are dissolved in a sufficient quantity of tetrahydrofuran, and this solution is then added to an ethanolic solution of sodium ethylate obtained from 1 gram (43.50 mmol) of sodium in approximately 150 ml of ethanol. The mixture is evaporated under vacuum and the residue is taken up with a sufficient quantity of dimethylformamide to dissolve it.

Stage B:
3-(2-Bromoethyl)-3H-Oxazolo[4,5-b]Pyridin-2-One 7.6 ml (88.22 mmol) of 1,2-dibromoethane, dissolved in approximately 50 ml of dimethylformamide, are placed in a round-bottomed flask under argon, surmounted by a condenser, and the solution obtained in the preceding step is then added slowly with stirring. The mixture is brought to 100° C. for 2 hours.

After cooling, the dimethylformamide is evaporated under vacuum and the residue is then taken up with water and extracted with methylene chloride. After drying over MgSO$_4$, the methylene chloride is evaporated off and the residue is purified on a flash silica column (230-240 mesh) in methylene chloride. After evaporation, 5.2 g of a white powder are obtained.

Yield: 50%

Preparation 4:
3-(3-Bromopropyl)-3H-Oxazolo[4,5-b]Pyridin-2-One

Using the procedure described in Preparation 3, but replacing 1,2-dibromoethane in stage B by 1,3-dibromopropane, the product of the title is obtained.

Preparation 5:
3-(4-Bromo-n-Butyl)-3H-Oxazolo[4,5-b]Pyridin-2-One

Using the procedure described in Preparation 3, but replacing 1,2-dibromoethane in stage B by 1,4-dibromo-n-butane, the product of the title is obtained.

Yield: 50%
Melting point: 46° C.
Spectral characteristics:

$^1$NMR Solvent CDCl$_3$: δ ppm δ: 1.92-2.09 ppm, multiplet; 4H; —CH$_2$—CH$_2$—CH$_2$—CH$_2$—Br δ: 3.47 ppm; triplet; 2H; CH$_2$—Br δ: 3.99 ppm; triplet; 2H δ: 7.06 ppm; doublet of doublet; 1H; H$_6$; JH$_6$H$_7$=8.3 Hz JH$_6$H$_6$=6.4 Hz δ: 7.40 ppm; doublet of doublet; 1H; H$_7$; JH$_7$H$_6$=8.3 Hz JH$_7$H$_5$=1 Hz δ: 8.11 ppm; doublet of doublet; 1H; H$_5$; JH$_5$H$_6$=5.3 Hz JH$_5$H$_7$=1 Hz

Preparation 6:
5-Methyl-3-(2-Bromoethyl)-3H-Oxazolo[4,5-b]Pyridin-2-One

Using the procedure described in Preparation 3, but replacing 3H-oxazolo[4,5-b]pyridin-2-one by 5-methyl-3H-oxazolo[4,5-b]pyridin-2-one, the product of the title is obtained.

EXAMPLE 1:
3-(2-PIPERIDINOETHYL)-3H-OXAZOLO[4,5-b]PYRIDIN-2-ONE 0.01 mol of 3-(2-bromoethyl)-3H-oxazolo[4,5-b]pyridin-2-one, dissolved in acetonitrile, 0.15 mol of piperidine and 0.015 mol of diisopropylethylamine are introduced into a round-bottomed flask placed under argon and surmounted by a condenser. The mixture is brought to 80° C. for 12 hours. It is cooled, the acetonitrile is evaporated off under vacuum and the residue is taken up with water. The alkalinity of the medium is checked and the medium is extracted with dichloromethane. The organic phase is dried over magnesium sulfate and evaporated and the residue is recrystallized.

Yield: 97%
Melting point: 84° C.
Spectral characteristics:

Infrared: 3100-2700 cm$^{-1}$, ν (CH) 1760 cm$^{-1}$, ν (C=O) 1590 cm$^{-1}$, ν (C=C) conjugated Nuclear magnetic resonance:

$^1$H NMR Solvent CDCl$_3$: δ ppm δ: 1.34-1.56, 6H; multiplet; piperidine (β and γ to the nitrogen) δ: 2.42-2.55, 4H; multiplet; piperidine (α to the nitrogen) δ: 2.76, 2H; triplet; piperidine CH$_2$—CH$_2$; J=4.1 Hz δ: 4.07, 2H; triplet; CH$_2$—CH$_2$; piperidine; J=6.1 Hz δ: 7.03 ppm: 1H; doublet of doublet; aromatic; H$_6$ δ: 8.09 ppm: 1H; doublet of doublet; aromatic; H$_5$

EXAMPLE 2:
3-[2-(4-METHYL-1-PIPERAZINYL)ETHYL]-3H-OXAZOLO[4,5-b]PYRIDIN-2-ONE

Using the procedure described in Example 1, but replacing piperidine by 1-methylpiperazine, the product of the title is obtained.

Yield: 90%
Melting point: 85° C.
Spectral characteristics:

Infrared: 3100-2700 cm$^{-1}$, ν (CH) 1760 cm$^{-1}$, ν (C=O) 1590 cm$^{-1}$, ν (C=C) conjugated Nuclear magnetic resonance:

$^1$H NMR Solvent CDCl$_3$: δ ppm δ: 2.23, singlet; 3H; CH$_3$ δ: 2.25-2.70, multiplet; 8H; piperazine δ: 2.79, 2H; triplet; piperazine CH$_2$—CH$_2$ δ: 4.05, 2H; triplet; piperazine CH$_2$—CH$_2$ δ: 7.04: 1H; doublet of doublet; aromatic; H$_6$ δ: 7.39: 1H; doublet of doublet; aromatic; H$_7$ δ: 8.09 1H; doublet of doublet; aromatic; H$_5$

EXAMPLE 3:
3-[2-(1-PYRROLIDINYL)ETHYL]-3H-OXAZOLO[4,5-b]PYRIDIN-2-ONE (OXALATE)

Using the procedure described in Example 1, but replacing piperidine by pyrrolidine, the product of the title is obtained in the form of a base. The product is dissolved in ethanol and 0.01 mol of oxalic acid is added. The product is drained.

Melting point: 180° C.
Spectral characteristics:

Infrared: 3100-2700 cm$^{-1}$, ν (CH) 1760 cm$^{-1}$, ν (C=O) 1590 cm$^{-1}$, ν (C=C)

Nuclear magnetic resonance:

$^1$H NMR Solvent CDCl$_3$: δ ppm δ: 7.04: 1H; doublet of doublet; aromatic; H$_6$ δ: 7.39: 1H; doublet of doublet; aromatic; H$_7$ δ: 8.09 1H; doublet of doublet; aromatic; H$_5$

EXAMPLE 4:
3-(2-MORPHOLINOETHYL]-3H-OXAZOLO[4,5-b]PYRIDIN-2-ONE

Using the procedure described in Example 1, but replacing piperidine by morpholine, the product of the title is obtained.

Yield: 98%
Melting point: 83° C.
Spectral characteristics:
Infrared: 3100–2700 cm$^{-1}$, $\nu$ (CH) 1760 cm$^{-1}$, $\nu$ (C=O) 1590 cm$^{-1}$, $\nu$ (C=C)
Nuclear magnetic resonance:
$^1$H NMR Solvent CDCl$_3$: δ ppm δ: 2.49–2.53: 4H; multiplet; 2 CH$_2$ α to the nitrogen:morpholine δ: 2.68: 2H; CH$_2$—CH$_2$—morpholine; J=6.3 Hz δ: 3.54–3.58: 4H; multiplet; 2CH$_2$ α to the oxygen; morpholine δ: 4.04: 2H; triplet; CH$_2$—morpholine; J=6.3 Hz δ: 7.03: 1H; doublet of doublet; aromatic; H$_6$ δ: 7.38: 1H; doublet of doublet; aromatic; H$_7$ δ: 8.08: 1H; doublet of doublet; aromatic; H$_5$

EXAMPLE 5:
3-(2-AMINOETHYL)-3H-OXAZOLO[4,5-b]PYRIDIN-2-ONE (HYDROCHLORIDE)

0.013 mol of hexamethylenetetramine, dissolved beforehand in 20 cm$^3$ of chloroform, and 0.01 mol of 3-(2-bromoethyl)-3H-oxazolo[4,5-b]pyridin-2-one, dissolved beforehand in 15 cm$^3$ of chloroform, are introduced into a round-bottomed flask placed under argon and surmounted by a condenser. The mixture is heated to reflux for one week. The product is drained and dried. The precipitate is introduced into a ground-necked 250-cm$^3$ flask equipped with a reflux condenser, and 50 cm$^3$ of absolute alcohol and 10 cm$^3$ of concentrated hydrochloric acid are added. The mixture is heated to reflux for two hours with magnetic stirring. The solvent is evaporated off on a water bath under vacuum and the product is recrystallized in alcohol at 95° C.

Yield: 70%
Spectral characteristics:
Infrared: 3200–2400 cm$^{-1}$, $\nu$ (NH) and $\nu$ (CH)
Nuclear magnetic resonance:
$^1$H NMR Solvent CDCl$_3$: δ ppm δ: 7.05 ppm: 1H; aromatic; H$_6$ δ: 7.38 ppm: 1H; aromatic; H$_7$ δ: 8.09 ppm: 1H; aromatic; H$_5$

EXAMPLE 6:
3-[2-(N-METHYL-N-BENZYLAMINO)ETHYL]-3H-OXAZOLO[4,5-b]PYRIDIN-2-ONE

Using the procedure described in Example 1, but replacing piperidine by N-methyl-N-benzylamine, the product of the title is obtained.

Yield: 75%
Spectral characteristics:
Infrared: 3100–2700 cm$^{-1}$, $\nu$ (CH) 1760 cm$^{-1}$, $\nu$ (C=O)
Nuclear magnetic resonance:
$^1$H NMR Solvent CDCl$_3$: δ ppm δ: 2.20 ppm; singlet: 3H; CH$_3$ δ: 7.03 ppm: 1H; H$_6$ δ: 7.38 ppm: 1H; H$_7$ δ: 8.09 ppm: 1H; H$_5$ δ: 7.27 ppm: 5H; aromatic (C$_6$H$_5$—CH$_2$)

EXAMPLE 7:
3-[2-(METHYLAMINO)ETHYL]-3H-OXAZOLO[4,5-b]PYRIDIN-2-ONE

In a 1,000-cm$^3$ ground-necked flask, 0.02 mol of 3-[2-(N-methyl-N-benzylamino)ethyl]-3H-oxazolo[4,5-b]pyridin-2-one is dissolved in 250 cm$^3$ of methanol. 0.2 g of palladinized charcoal is introduced and the mixture is stirred under a hydrogen atmosphere at room temperature and atmospheric pressure. After absorption of the theoretical quantity of hydrogen, the reaction medium is filtered. The filtrate is concentrated on a water bath under vacuum and acidified with a stream of gaseous hydrochloric acid. The precipitate obtained is drained, dried and recrystallized.

Yield: 75%
Spectral characteristics:
Infrared: 3100–2600 cm$^{-1}$, $\nu$ (NH) or $\nu$ (CH) 2440 cm$^{-1}$, $\nu$ (NH) 1750 cm$^{-1}$, $\nu$ CO (OCON) 1610 cm$^{-1}$, $\nu$ (C=C) aromatic
Nuclear magnetic resonance:
$^1$H NMR Solvent CDCl$_3$: δ ppm δ: 7.05 ppm, doublet of doublet; 1H; H$_6$ δ: 7.38 ppm; doublet of doublet; 1H; H$_7$ δ: 8.09 ppm, doublet of doublet; 1H; H$_5$

EXAMPLE 8:
3-[2-(ISOPROPYLAMINO)ETHYL]-3H-OXAZOLO[4,5-b]PYRIDIN-2-ONE (HYDROBROMIDE)

0.1 mol of isopropylamine and 0.01 mol of 3-(2-bromoethyl)-3H-oxazolo[4,5-b]pyridin-2-one, dissolved beforehand in 40 cm$^3$ of acetonitrile, are introduced into a 100-cm$^3$ ground-necked round-bottomed flask equipped with a reflux condenser. The mixture is heated to reflux for 15 hours. After cooling, the precipitate obtained is drained, dried and recrystallized.

Yield: 92%
Spectral charcteristics:
Infrared: 3100–2650 cm$^{-1}$, $\nu$ (NH) and $\nu$ (CH) 2450 cm$^{-1}$, $\nu$ (NH) 1745 cm$^{-1}$, $\nu$ CO

EXAMPLE 9:
3-[2-(CYCLOPROPYLAMINO)ETHYL]-3H-OXAZOLO[4,5-b]PYRIDIN-2-ONE (HYDROBROMIDE)

Using the procedure described in Example 8, but replacing isopropylamine by cyclopropylamine, the product of the title is obtained.

EXAMPLE 10:
3-[2-(DIETHYLAMINO)ETHYL]-3H-OXAZOLO4,5-b]PYRIDIN-2-ONE (OXALATE)

Using the procedure described in Example 1, but replacing piperidine by diethylamine, the product of the title is obtained in the form of a base. It is dissolved in ethanol and 0.01 mol of oxalic acid is added. The product is drained. It is dried. It is recrystallized.

Melting point: 139° C.

EXAMPLE 11:
3-[2-(N-METHYL-N-CYCLOHEXYLAMINO)ETHYL]-3H-OXAZOLO[4,5-b]PYRIDIN-2-ONE

Using the procedure described in Example 1, but replacing piperidine by N-methyl-N-cyclohexylamine, the product of the title is obtained.

EXAMPLE 12:
3-[2-(4-PHENYLPIPERIDINO)ETHYL]-3H-OXAZOLO[4,5-b]PYRIDIN-2-ONE

Using the procedure described in Example 1, but replacing piperidine by 4-phenylpiperidine, the product of the title is obtained.

Melting point: 88° C.

EXAMPLE 13:
3-[2-(1,2,3,4-TETRAHYDRO-1-QUINOLYL)E-THYL]-3H-OXAZOLO[4,5-b]PYRIDIN-2-ONE

Using the procedure described in Example 1, but replacing piperidine by 1,2,3,4-tetrahydroquinoline, the product of the title is obtained.

EXAMPLE 14:
3-MORPHOLINOMETHYL-3H-OXAZOLO[4,5-b]PYRIDIN-2-ONE 4.1 g (0.03 mol) of 3H-oxazolo[4,5-b]pyridin-2-one are dissolved in 100 ml of alcohol at 95° C. 2.88 g (0.33 mol) of morpholine and then 3 ml of 30% aqueous formaldehyde solution are added. The mixture is stirred on a water bath at a temperature in the region of 50° C. for one hour 30 minutes, stirring being maintained. The mixture is left to stand for one hour at room temperature. The crystals are drained and recrystallized.

Yield: 85%

Spectral characteristics:

Infrared: 3100-2700 cm$^{-1}$, $\nu$ (CH) 1760 cm$^{-1}$, $\nu$ (CO) 1590 cm$^{-1}$, $\nu$ (C=C)

EXAMPLE 15:
3-(1-PYRROLIDINYLMETHYL)-3H-OXAZOLO[4,5-b]PYRIDIN-2-ONE

Using the procedure described in Example 14, but replacing morpholine by pyrrolidine, the product of the title is obtained.

EXAMPLE 16:
3-PIPERIDINOMETHYL-3H-OXAZOLO[4,5-b]PYRIDIN-2-ONE

Using the procedure described in Example 14, but replacing morpholine by piperidine, the product of the title is obtained.

EXAMPLE 17:
3-(2-PIPERIDINOETHYL)-5-METHYL-3H-OXAZOLO[4,5-b]PYRIDINE-2-ONE

Using the procedure described in Example 1, but replacing 3-(2-bromoethyl)-3H-oxazolo[4,5-b]pyridin-2-one by 3-(2-bromoethyl)-5-methyl-3H-oxazolo[4,5-b]pyridin-2-one obtained in Preparation 6, the product of the title is obtained.

EXAMPLE 18:
3-[2-(4-TRIFLUOROMETHYLBENZYLAMINO)E-THYL]-3H-OXAZOLO[4,5-b]PYRIDIN-2-ONE

Using the procedure described in Example 1, but replacing piperidine by 4-trifluoromethylbenzylamine, the product of the title is obtained.

EXAMPLE 19:
3-[2-(4-METHYLPIPERIDINO)ETHYL]-3H-OXAZOLO[4,5-b]PYRIDIN-2-ONE

Using the procedure described in Example 1, but replacing piperidine by 4-methylpiperidine, the product of the title is obtained.

EXAMPLE 20:
3-[2-(4-BENZYLPIPERIDINO)ETHYL]-3H-OXAZOLO[4,5-b]PYRIDIN-2-ONE

Using the procedure described in Example 1, but replacing piperidine by 4-benzylpiperidine, the product of the title is obtained.

EXAMPLE 21:
3-[2-(2-CHLOROETHYLAMINO)ETHYL]-3H-OXAZOLO[4,5-b]PYRIDIN-2-ONE

Using the procedure described in Example 1, but replacing piperidine by 2-chloroethylamine, the product of the title is obtained.

EXAMPLE 22:
3-{2-[4-(4,4'-DIFLUOROBENZHYDRYL)-1-PIPERAZINYL]ETHYL}-3H-OXAZOLO[4,5-b]PYRIDIN-2-ONE

Using the procedure described in Example 1, but replacing piperidine by 1-(4,4'-difluorobenzhydryl)piperazine, the product of the title is obtained.

EXAMPLE 23:
3-[2-(4-BENZHYDRYL-1-PIPERAZINYL)E-THYL]-3H-OXAZOLO[4,5-b]PYRIDIN-2-ONE

Using the procedure described in Example 1, but replacing piperidine by 1-benzhydrylpiperzine, the product of the title is obtained.

EXAMPLE 24:
3-{2-[4-(4-CHLOROBENZHYDRYL)-1-PIPERAZINYL]ETHYL}-3H-OXAZOLO[4,5-b]PYRIDIN-2-ONE

Using the procedure described in Example 1, but replacing piperidine by 1-(4-chlorobenzhydryl)piperazine,

EXAMPLE 25:
2-(2-PIPERIDINOETHYLAMINO)-3-PYRIDINOL 0.01 mol of 3-(2-piperidinoethyl)-3H-oxazolo[4,5-b]pyridin-2-one, obtained in Example 1, is placed in 50 ml of 10% sodium hydroxide solution. The mixture is heated to reflux for 4 hours with magnetic stirring. After cooling, the solution is acidified with 30% hydrochloric acid. While cooling, saturated aqueous sodium bicarbonate solution is added until the pH=7. The precipitate is filtered off and washed three times with water, dried under vacuum in a desiccator and then washed again.

By using the procedure described in Example 25, but employing the compounds obtained in Examples 2 to 24 as starting material, 2-{[(substituted)amino]alkylamino}-3-pyridinols, substituted where appropriate, are obtained.

PHARMACOLOGICAL STUDY OF THE COMPOUNDS OF THE INVENTION

EXAMPLE 26: STUDY OF THE ACUTE TOXICITY

The toxicity was assessed after oral administration of increasing doses (0.1, 0.25, 0.50, 0.75 and 1 g/kg) to batches of five mice (20±2 grams). The animals were observed at regular intervals during the first day, and daily during the two weeks following the treatment.

It is apparent that the compounds of the invention are completely non-toxic.

EXAMPLE 27: STUDY OF THE ANALGESIC ACTIVITY

The activity against pain was investigated in mice (23-25 g) according to a protocol derived from the technique described by SIEGMUND (SIEGMUND E. A., R. A. CADMUS & GOLU, J. Pharm. Exp. Ther.

119, 184, 1957). The mice, randomized in batches of 12 animals, received the treatment orally (excipient for the controls) 1 hour before the intraperitoneal injection of a 0.02% aqueous-alcoholic solution of phenyl-p-benzoquinone. The writhing movements are counted between the 5th and 10th minute after injection.

The percentage activity obtained was evaluated for each dose (% decrease in the number of writhing movements in the treated animals relative to the controls). An $ED_{50}$, the dose producing a 50% activity, was determined for each product tested.

EXAMPLE 28: STUDY OF THE ANTI-INFLAMMATORY ACTIVITY

The anti-inflammatory potential of the compounds was investigated on a model of acute inflammation induced by the subcutaneous injection of a solution of carrageenan into the rat hind foot, according to a technique based on the method of WINTER, C. A., E. A. RISLEY and G. N. NUSS—Proc. Soc. Exp. Med. 111, 554, 1962. The rats (100–120 g), randomized in batches of 8, were treated (including the controls, which receive excipient) 1 hour before the local injection of a 0.5% suspension of carrageenan (Sigma type IV; 0.1 ml per rat). The edema is determined 3 hours after injection, by plethysmometric measurement (UGO BASILE water plethysmometer) of the volume of each of the hind feet (edema = volume of the inflamed foot—volume of the non-inflamed foot).

The percentage activity corresponds to the percentage decrease in the mean edema of the batch compared to the mean of the corresponding control batch. An $ED_{30}$, the dose producing a 30% activity, was determined.

This $ED_{30}$ is equal to 50 mg.kg$^{-1}$ for the compound of Example 6 of U.S. Pat. No. 4,038,396. It is very markedly greater than this value for all the compounds of the invention; up to a dose of 150 mg/kg$^{-1}$, they have no anti-inflammatory activity.

EXAMPLE 29: GASTRIC TOLERANCE TEST

A group of 5 rats is subjected to fasting for 24 hours. The test products are administered orally, in suspension in acacia syrup at a dose of 150 mg.kg$^{-1}$. After administration, the animals are placed under so-called semi-constrained conditions reputed to be ulcerogenic (they are shut up in narrow cages. After 6 hours, they are sacrificed and the stomach wall is examined. Gastric tolerance is defined on the basis of the scoring of SHAY and LAMBLING. The severity of the irritated areas and of the points of ulceration is scored from 0 to 3. An index of ulceration U and an index of hyperemia or irritation H are defined.

$$U \text{ or } H = \frac{(\text{Sum of the scores}) \times (\text{number of points of stomach tested})}{\text{Number of animals studied}}$$

Overall index of propensity for attack $G = 3U + H$.

This index G is equal to 1 for the products of the invention, 12 for the control and 74 for aspirin.

EXAMPLE 30: TEST OF BINDING TO RECEPTORS

A study of the binding of the compounds of the invention to different categories of receptors was carried out according to conventional techniques. It is apparent that some compounds of the invention bind with good affinity ($10^{-7}M$) to MI muscarinic receptors, which does not appear to have been reported hitherto for comparable structures.

EXAMPLE 31: PHARMACEUTICAL COMPOSITION: TABLET

Tablets containing 25 mg of 3-(2-piperidinoethyl)-3H-oxazolo[4,5-b]pyridin-2-one

| Preparation formula for 1,000 tablets | |
|---|---|
| 3-[2-(1-Pyrrolidinyl)ethyl]-3H-oxazolo-[4,5-b]pyridin-2-one | 25 g |
| Wheat starch | 15 g |
| Corn starch | 15 g |
| Lactose | 65 g |
| Magnesium stearate | 1 g |
| Silica | 1 g |
| Hydroxypropoylcellulose | 2 g |

APPENDIX

Nomenclature

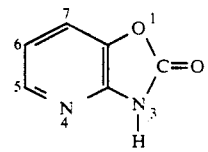

3H-OXAZOLO[4,5-b]PYRIDIN-2-ONE

We claim:
1. A compound selected from those of Formula (I)

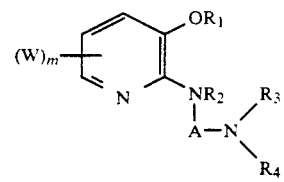

in which:
$R_1$ and $R_2$, with the nitrogen and oxygen to which connected, form an
—O—CO—N link,
W represents a halogen atom, or a lower alkyl or alkoxy group optionally substituted with one or more halogen atoms, m being 0 to 3, inclusive,
A is a linear or branched alkyl radical having 1 to 6 carbon atoms, inclusive,
$R_3$ and $R_4$, which may be identical or different, represent:
a hydrogen atom,
a linear or branched lower alkyl group,
a linear or branched lower alkenyl group,
a cycloalkyl group having 6 to 10 carbon atoms, inclusive,
an aryl or (lower alkyl)aryl group,
each of these groups being optionally substituted with one or more halogen atoms or with a trifluoromethyl, hydroxyl, or lower alkoxy group, or alternatively:
$R_3$ and $R_4$, with the nitrogen atom to which they are linked, constitute a saturated or unsaturated, mono- or bicyclic nitrogenous heterocyclic system having at most 12 atoms—not counting the hydrogen atoms—among which may be included one to three hetero atoms selected from nitrogen, oxygen and sulfur, unsubstituted or substituted with lower alkyl, phenyl, phenyl(lower alkyl), or diphenyl(lower alkyl) it being possible for the phenyl, phenyl(lower alkyl), or diphenyl(lower alkyl) group to be substituted with one or more halogen atoms or a hydroxyl, lower alkyl, lower alkoxy, or trifluoromethyl group, on condition that $R_3$ and $R_4$, with the nitrogen atom to which they are linked, do not constitute a 4-arylpiperazine system, the terms lower alkyl, lower alkenyl, and lower alkoxy being understood to mean a linear or branched group having 1 to 6 carbon atoms, inclusive, and aryl being understood to mean an unsaturated mono- or bicyclic group having 5 to 12 carbon atoms, inclusive, its isomers, epimers and diastereoisomers, as well as its addition salts with a pharmaceutically-acceptable acid, provided however that, when m represents zero and A represents —$CH_2$— or when m represents one and W represents halogen, then $R_3$ and $R_4$ with the nitrogen atom to which they are linked, constitute a saturated or unsaturated, mono- or bicyclic nitrogenous heterocyclic system having at most 12 atoms—not counting the hydrogen atoms— among which may be included one to three hetero atoms selected from nitrogen, oxygen and sulfur, unsubstituted or substituted with a lower alkyl, phenyl, phenyl(lower alkyl), or diphenyl(lower alkyl) it being possible for the phenyl, phenyl(lower alkyl), or diphenyl(lower alkyl) group to be substituted with one or more halogen atoms or a hydroxyl, lower alkyl, lower alkoxy, or trifluoromethyl group, on condition that $R_3$ and $R_4$, with the nitrogen atom to which they are linked, do not constitute a 4-arylpiperazine system.

2. A compound as claimed in claim 1 selected from those in which $R_1$ and $R_2$ together form a CO group, of formula (I/A):

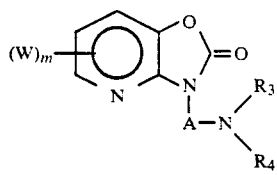

(I/A)

as well as its addition salts with a pharmaceutically acceptable acid.

3. A compound as claimed in claim 1 selected from those in which $R_3$ and $R_4$, with the nitrogen atom which bears them, represent a saturated mono- or bicyclic nitrogenous heterocyclic system having 5 to 12 atoms not counting the hydrogen atoms optionally incorporating in its carbon skeleton 1, 2 or 3 hetero atoms selected from nitrogen, oxygen, and sulfur, its isomers, epimers and diastereoisomers, as well as its addition salts with a pharmaceutically acceptable acid.

4. The compound as claimed in claim 1 which is selected from 3-(2-piperidinoethyl)-3H-oxazolo[4,5-b]pyridin-2-one, as well as its addition salts with a pharmaceutically acceptable acid.

5. The compound as claimed in claim 1 which is selected from 3-[2-(4-methyl-1-piperazinyl)ethyl]-3H-oxazolo[4,5-b]pyridin-2-one, as well as its addition salts with a pharmaceutically acceptable acid.

6. The compound as claimed in claim 1 which selected from 3-[2-(1-pyrrolidinyl)ethyl]-3H-oxazolo[4,5-b]pyridin-2-one, as well as its addition salts with a pharmaceutically acceptable acid.

7. The compound as claimed in claim 1 which is selected from 3-(2-morpholinoethyl)-3H-oxazolo[4,5-b]pyridin-2-one, as well as its addition salts with a pharmaceutically acceptable acid.

8. A pharmaceutical composition useful for treating cerebral circulatory insufficiency containing as active principle a compound selected from those of Formula (I)

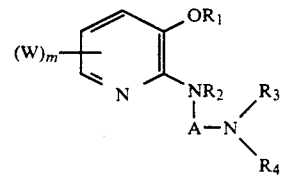

in which:
$R_1$ and $R_2$, with the nitrogen and oxygen to which connected, form an
—O—CO—N link,
W represents a halogen atom or a lower alkyl or alkoxy group optionally substituted with one or more halogen atoms, m being 0 to 3, inclusive,
A is a linear or branched alkyl radical having 1 to 6 carbon atoms, inclusive,
$R_3$ and $R_4$, which may be identical or different, represent:
a hydrogen atom,
a linear or branched lower alkyl group,
a linear or branched lower alkenyl group,
a cycloalkyl group having 6 to 10 carbon atoms, inclusive,
an aryl or (lower alkyl)aryl group,
each of these groups being optionally substituted with one or more halogen atoms or with a trifluoromethyl, hydroxyl, or lower alkoxy group, or alternatively:
$R_3$ and $R_4$, with the nitrogen atom to which they are linked, constitute a saturated or unsaturated, mono- or bicyclic nitrogenous heterocyclic system having at most 12 atoms—not counting the hydrogen atoms—among which may be included one to three hetero atoms selected from nitrogen, oxygen and sulfur, unsubstituted or substituted with lower alkyl, phenyl, phenyl(lower alkyl), or diphenyl(lower alkyl), it being possible for the phenyl, phenyl(lower alkyl), or diphenyl(lower alkyl) group to be substituted with one or more halogen atoms or a hydroxyl, lower alkyl, lower alkoxy, or trifluoromethyl group, on condition that $R_3$ and $R_4$, with the nitrogen atom to which they are linked, do not constitute a 4-arylpiperazine system, the terms lower alkyl, lower alkenyl, and lower alkoxy being understood to mean a linear or branched group having 1 to 6 carbon atoms, inclusive, and aryl groups being understood to mean an unsaturated mono- or bicyclic group having 5 to 12 carbon atoms, inclusive, its isomers, epimers and diastereoisomers, as well as its addition salts with a pharmaceutically-acceptable acid, in combination with a pharmaceutically-acceptable excipient or vehicle.

9. A method-of-treating a living animal afflicted with a disorder of cerebral circulatory insufficiency comprising the step of administering to the said living animal an amount of a compound selected from those of Formula (I)

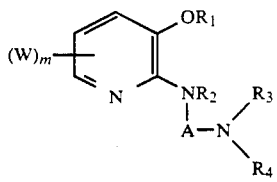

in which:
- $R_1$ and $R_2$, with the nitrogen and oxygen to which connected, form an
  —O—CO—N link,
- W represents a halogen atom or a lower alkyl or alkoxy group optionally substituted with one or more halogen atoms, m being 0 to 3, inclusive,
- A is a linear or branched alkyl radical having 1 to 6 carbon atoms, inclusive,
- $R_3$ and $R_4$, which may be identical or different, represent:
  - a hydrogen atom,
  - a linear or branched lower alkyl group,
  - a linear or branched lower alkenyl group,
  - a cycloalkyl group having 6 to 10 carbon atoms, inclusive,
  - an aryl or (lower alkyl)aryl group, each of these groups being optionally substituted with one or more halogen atoms or with a trifluoromethyl, hydroxyl, or lower alkoxy group, or alternatively:
- $R_3$ and $R_4$, with the nitrogen atom to which they are linked, constitute a saturated or unsaturated, mono- or bicyclic nitrogenous heterocyclic system having at most 12 atoms—not counting the hydrogen atoms—among which may be included one to three hetero atoms selected from nitrogen. oxygen and sulfur, unsubstituted or substituted with lower alkyl, phenyl, phenyl(lower alkyl), or diphenyl(lower alkyl), it being possible for the phenyl, phenyl(lower alkyl), or diphenyl(lower alkyl) group to be substituted with one or more halogen atoms or a hydroxyl, lower alkyl, lower alkoxy, or trifluoromethyl group, on condition that $R_3$ and $R_4$, with the nitrogen atom to which they are linked, do not constitute a 4-arylpiperazine system, the terms lower alkyl, lower alkenyl, and lower alkoxy being understood to mean a linear or branched group having 1 to 6 carbon atoms, inclusive, and aryl groups being understood to mean an unsaturated mono- or bicyclic group having 5 to 12 carbon atoms, inclusive, its isomers, epimers and diastereoisomers, as well as its addition salts with a pharmaceutically-acceptable acid, which is effective for alleviation of said condition.

10. A compound of claim 1 wherein W represents a trifluoromethyl group.

11. A pharmaceutical composition of claim 8 wherein W represents a trifluoromethyl group.

12. A method of claim 9 wherein W represents a trifluoromethyl group.

13. A pharmaceutical composition of claim 8 wherein the compound is 3-[2-(1-pyrrolidinyl)ethyl]-3H-oxazolo[4,5-b]pyridin-2-one or a pharmaceutically-acceptable acid addition salt thereof.

14. A method of claim 9 wherein the compound is 3-[2-(1-pyrrolidinyl)ethyl]-3H-oxazolo[4,5-b]pyridin-2-one or a pharmaceutically-acceptable acid addition salt thereof.

* * * * *

UNITED STATES PATENT AND TRADEMARK OFFICE
CERTIFICATE OF CORRECTION

PATENT NO. : 5,155,116
DATED : Oct. 13, 1992
INVENTOR(S) : Gerald Guillaumet, Christine Flouzat, Daniel H.
Caignard, Pierre Renard, Michelle Devissaguet, Béatrice Guardiola It is certified that error appears in the above-identified patent and that said Letters Patent is hereby corrected as shown below:

Column 1, approximately line 15; "analogesic" should read -- analgesic --.
Column 1, approximately line 25; "posses" should read --possess--.
Column 2, approximately line 17; "bicycle" should read -- bicyclic--.
Column 4, approximately line 17; "D'," should read -- X', --.
Column 6, line 41/42; "Preparation should read --Preparation 2:
    2:15 Methyl-"                    5- Methyl- --
Column 7, line 56; "$^1$NMR" should read --$^1$H NMR --.
Column 7, line 60; "JH$_6$H$_6$" should read -- JH$_6$H$_5$ --.
Column 8, line 29,30 "aromatic:H$_6$ δ: 8.09" should read --aromatic; H$_6$δ : 7.38 ppm: 1H; doublet of doublet; aromatic; H$_7$ δ 8.09 --.
Column 8, line 52; "OXAZX-" should read -- OXAZ- --
Column 10, line 46; "OXAZOLO4,5-b] should read --OXAZOLO[4,5-b] --.
Column 12, approximately line 30; "zine," should read -- zine, the product of the title is obtained. --.
Column 13, line 47; "cages." should read -- cages). --.
Column 14, line 28, 29;

reads " 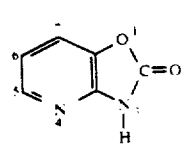    should read -- 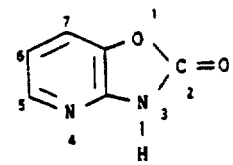 --

Signed and Sealed this

Twenty-third Day of November, 1993

Attest:

BRUCE LEHMAN

Attesting Officer      Commissioner of Patents and Trademarks